(12) United States Patent
Ostermeier et al.

(10) Patent No.: US 8,263,768 B2
(45) Date of Patent: Sep. 11, 2012

(54) PROCESS FOR THE STEREOSELECTIVE PREPARATION OF BICYCLIC HETEROCYCLES

(75) Inventors: Markus Ostermeier, Biberach (DE);
Stefan Braith, Warthausen (DE);
Juergen Daeubler, Ummendorf (DE);
Guenther Huchler, Hochdorf (DE);
Waldemar Pfrengle, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/057,871

(22) PCT Filed: Jul. 23, 2009

(86) PCT No.: PCT/EP2009/059512
§ 371 (c)(1),
(2), (4) Date: Mar. 24, 2011

(87) PCT Pub. No.: WO2010/015524
PCT Pub. Date: Feb. 11, 2010

(65) Prior Publication Data
US 2012/0116080 A1    May 10, 2012

(30) Foreign Application Priority Data
Aug. 8, 2008  (EP) .................................. 08104993

(51) Int. Cl.
*C07D 239/72*  (2006.01)
*C07D 241/00*  (2006.01)

(52) U.S. Cl. ....................... 544/283; 544/336

(58) Field of Classification Search .................. 544/283, 544/336
See application file for complete search history.

(56) References Cited

U.S. PATENT DOCUMENTS

| | | |
|---|---|---|
| 2005/0215574 A1 | 9/2005 | Bradbury et al. |
| 2008/0269487 A1 | 10/2008 | Bradbury et al. |
| 2010/0022505 A1 | 1/2010 | Himmelsbach et al. |
| 2010/0152442 A1 | 6/2010 | Bradbury et al. |

FOREIGN PATENT DOCUMENTS

| | | |
|---|---|---|
| CA | 2669187 A1 | 5/2008 |
| EP | 1921070 A | 5/2008 |
| WO | 03082831 A | 10/2003 |
| WO | 2008095847 A | 8/2008 |

OTHER PUBLICATIONS

International Search Report dated Sep. 14, 2009, corresponding to PCT Application No: PCT/EP2009/059512 and English translation thereof.

*Primary Examiner* — Paul V. Ward
(74) *Attorney, Agent, or Firm* — Michael P. Morris; Edward S. Lazer

(57) ABSTRACT

The present invention relates to a process for the stereoselective preparation of compounds of general formula (I)

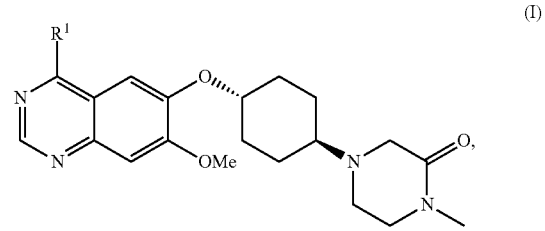

(I)

and the salts thereof, particularly the physiologically acceptable salts thereof with inorganic or organic acids and bases, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways.

10 Claims, No Drawings

PROCESS FOR THE STEREOSELECTIVE PREPARATION OF BICYCLIC HETEROCYCLES

The present invention relates to a process for the stereoselective preparation of compounds of general formula (I)

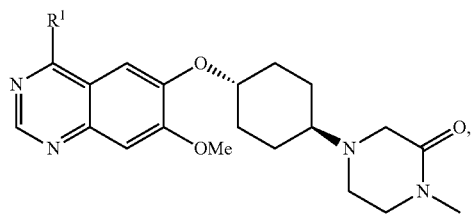
(I)

and the salts thereof, particularly the physiologically acceptable salts thereof with inorganic or organic acids and bases, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways.

BACKGROUND TO THE INVENTION

Quinazoline derivatives are known from the prior art as active substances for example for the treatment of tumoral diseases and also diseases of the lungs and airways. Processes for preparing quinazoline derivatives are described in WO03082831.

The problem of the present invention is to prepare a stereoselective process for preparing the quinazoline derivatives according to the invention.

DESCRIPTION OF THE INVENTION

The present invention solves the above-mentioned problem by the method of synthesis described hereinafter.

The invention thus relates to a process for the stereoselective preparation of compounds of general formula (I),

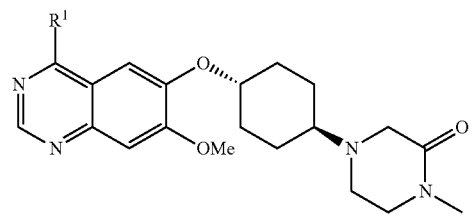
(I)

optionally in the form of the tautomers thereof, and optionally the pharmacologically acceptable acid addition salts thereof, wherein $R^1$ denotes a group selected from among 3-chloro-2-fluoro-phenyl-amino, 3-chloro-4-fluoro-phenylamino, 2-fluoro-3-methyl-phenylamino, 2,5-difluoro-3-methyl-phenylamino, 3-chloro-2-methyl-phenylamino and 2-fluoro-5-methyl-phenylamino, preferably 3-chloro-2-fluoro-phenyl-amino or 3-chloro-4-fluoro-phenylamino, particularly preferably 3-chloro-2-fluoro-phenyl-amino, the process comprising reaction steps (1a) to (1d), wherein (1a) is the reaction of a compound of formula (II)

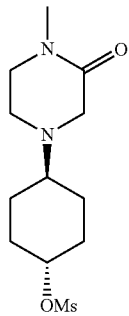
(II)

with a compound of formula (III)

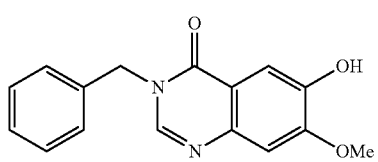
(III)

to obtain a compound of formula (IV)

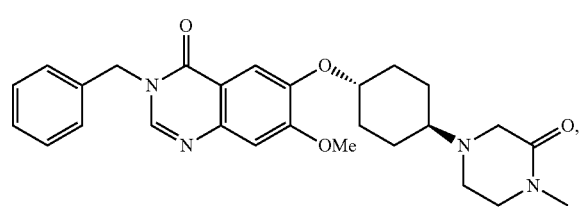
(IV)

(1b) is the cleaving of the benzyl group of the compound of formula (IV) in the presence of a catalyst to obtain a compound of formula (V)

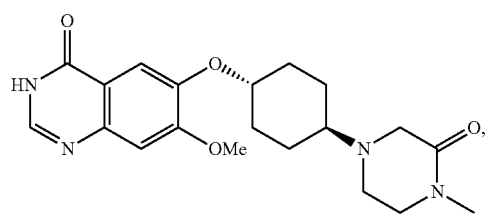
(V)

(1c) is the reaction of the compound of formula (V) with a chlorinating agent to obtain the hydrochloride of a compound of formula (VI)

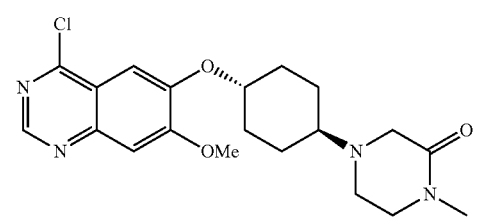
(VI)

and
(1d) is the reaction of the compound of formula (VI) with one of the compounds (i) to (vi) to obtain a compound of formula (I), wherein (i) is 3-chloro-2-fluoro-aniline,
(ii) is 3-chloro-4-fluoro-aniline,
(ii) is 2-fluoro-3-methyl-aniline,
(iii) is 2,5-difluoro-3-methyl-aniline,
(iv) is 3-chloro-2-methyl-aniline, and
(vi) is 2-fluoro-5-methyl-aniline,
preferably 3-chloro-2-fluoro-aniline or 3-chloro-4-fluoro-aniline, particularly preferably 3-chloro-2-fluoro-aniline,
while steps (1a) to (1d) are carried out successively in the order specified,
or
wherein the process comprises reaction steps (2a), (1c) and (1d), wherein (2a) is the reaction of a compound of formula (II)

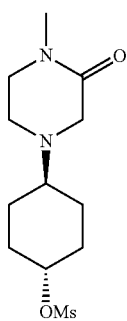
(II)

with a compound of formula (VII)

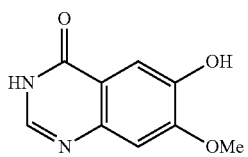
(VII)

to obtain a compound of formula (V)

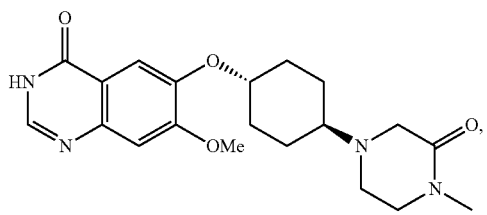
(V)

wherein the steps are carried out successively in the order stated.

Preferred is a process for the stereoselective preparation of compounds of general formula (I), wherein the process consists of process steps (1a) to (1d).

Also preferred is a process for the stereoselective preparation of compounds of general formula (I), wherein the process consists of process steps (2a), (1c) and (1d).

Also preferred is a process for the stereoselective preparation of compounds of general formula (IV), characterised in that the process consists of process step (1a).

Also preferred is a process for the stereoselective preparation of compounds of general formula (V), characterised in that the process consists of process step (1b).

Also preferred is a process for the stereoselective preparation of compounds of general formula (VI), characterised in that the process consists of process step (1c).

Also preferred is a process for the stereoselective preparation of compounds of general formula (I), characterised in that the process consists of process step (1d).

Also preferred is a process for the stereoselective preparation of compounds of general formula (IV), characterised in that the process consists of process step (2a).

Particularly preferred is a process wherein in process step (1b) a palladium/charcoal catalyst is used.

Also particularly preferred is a process wherein a chlorinating agent selected from among oxalyl chloride, thionyl chloride, phosphorus oxychloride, phosphorus pentachloride, an N-chlorosuccinimide/triphenylphosphane combination, a carbon tetrachloride/triphenylphosphane combination, dichlorotriphenylphosphoran and P,P-dichlorophenylphosphine oxide is used.

The invention further relates to the compound of formula (II).

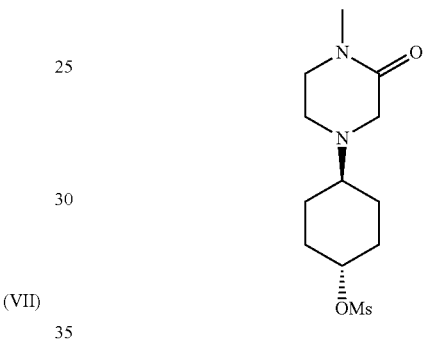
(II)

The invention further relates to the compound of formula (VIII).

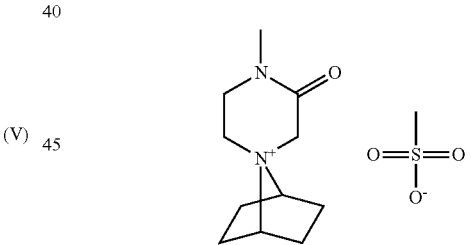
(VIII)

The compounds according to the invention may be present in the form of the tautomers as well as in the form of the free bases or the corresponding acid addition salts with pharmacologically acceptable acids—such as for example acid addition salts with hydrohalic acids, for example hydrochloric or hydrobromic acid, inorganic acids, for example phosphoric acid or sulphuric acid or organic acids, such as for example oxalic, fumaric, diglycolic, toluenesulphonic, benzoic, succinic or methanesulphonic acid.

Process step (1a) is preferably carried out in a solvent selected from among dimethylformamide (DMF), N-methyl-2-pyrrolidone (NMP), N-ethyl-2-pyrrolidone (NEP) and dimethylsulphoxide (DMSO), preferably in NMP.

Process step (1a) is preferably carried out in a temperature range of from 70° C. to 150° C., preferably from 100° C. to 145° C., particularly preferably at a temperature of 140° C.

In process step (1a) bases selected from among $Na_2CO_3$, $K_2CO_3$, $Cs_2CO_3$, preferably $Na_2CO_3$, are preferably used.

Process step (2a) is preferably carried out in a solvent selected from among DMF, NMP, NEP and DMSO, preferably in NMP.

Process step (2a) is preferably carried out in a temperature range of from 70° C. to 150° C., preferably from 100° C. to 140° C., particularly preferably at a temperature of 130° C.

Process step (1b) is preferably carried out in a solvent selected from among H₂O, HOAc, EtOH, n-PrOH, i-PrOH, amylalcohol and NMP, preferably in H₂O/HOAc. Process step (1b) is preferably carried out in a temperature range of from 0° C. to 140° C., preferably from 60° C. to 100° C., particularly preferably at a temperature of 80° C.

In process step (1b) catalysts selected from among Pd/C, Pd(OH)₂ preferably Pd/C, are preferably used.

Process step (1c) is preferably carried out in a solvent selected from among dioxane, acetonitrile, tetrahydrofuran (THF) and diethyleneglycol dimethylether, preferably in dioxane/acetonitrile.

Process step (1c) is preferably carried out in a temperature range of from 20° C. to 140° C., preferably from 70° C. to 130° C., particularly preferably at a temperature of 120° C.

Process step (1d) is preferably carried out in a solvent selected from among H₂O, HCl$_{aqueous}$, NMP and acetonitrile, preferably in HCl$_{aqueous}$.

In process step (1d) auxiliary acids selected from among HCl, H₂SO₄, H₃PO₄, MsOH and TsOH, preferably HCl, are preferably used.

Process step (1d) is preferably carried out in a temperature range of from 5° C. to 100° C., preferably from 10° C. to 40° C., particularly preferably at a temperature of 20° C.

Schemes 1 to 3 illustrate the synthesis according to the invention.

Scheme 1 Synthesis of (trans)-1-hydroxy-4-(4-methyl-3-oxo-piperazin-1-yl)-cyclohexane

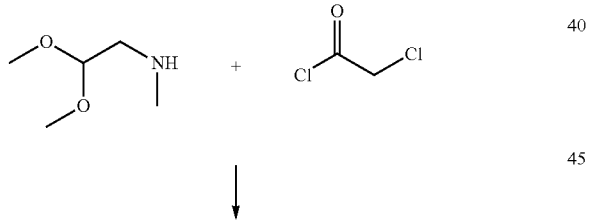

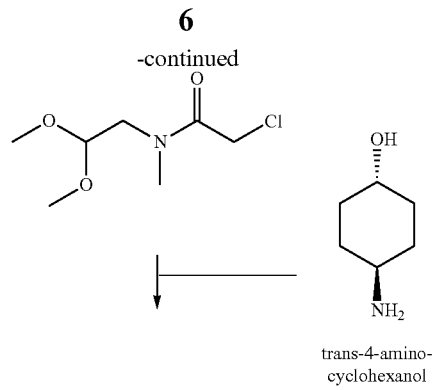

trans-4-amino-cyclohexanol

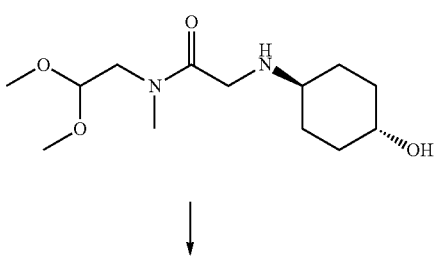

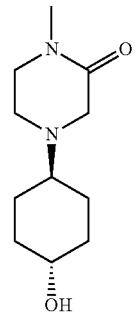

Scheme 2 Synthesis steps (1a), (1b), (1c) and (1d).

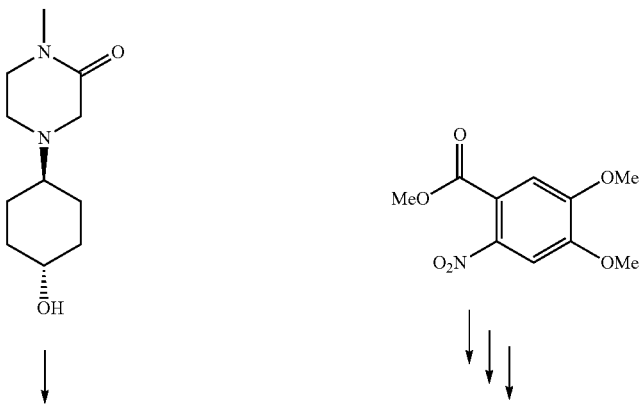

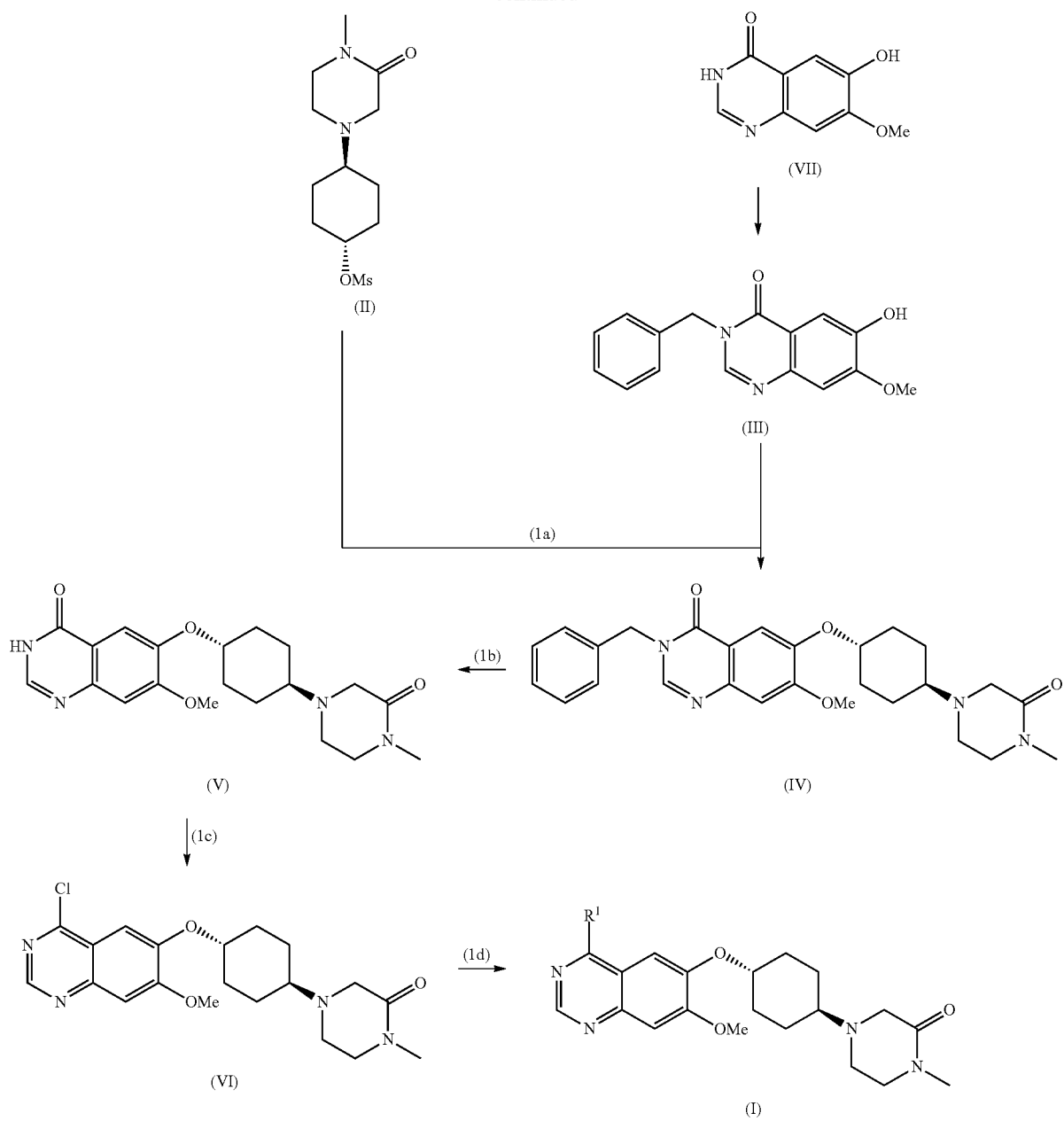
Scheme 3 Synthesis steps (2a), (1c) and (1d).
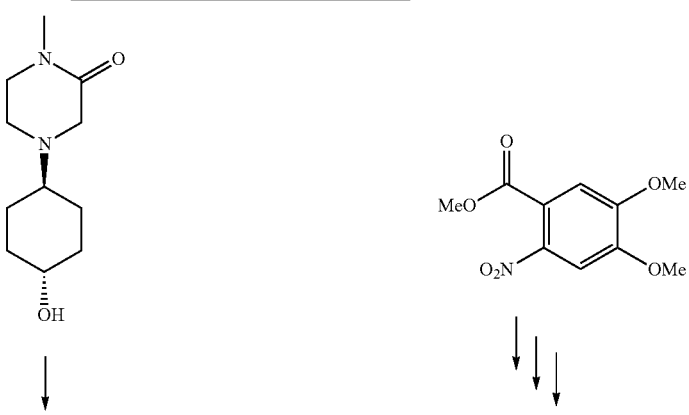

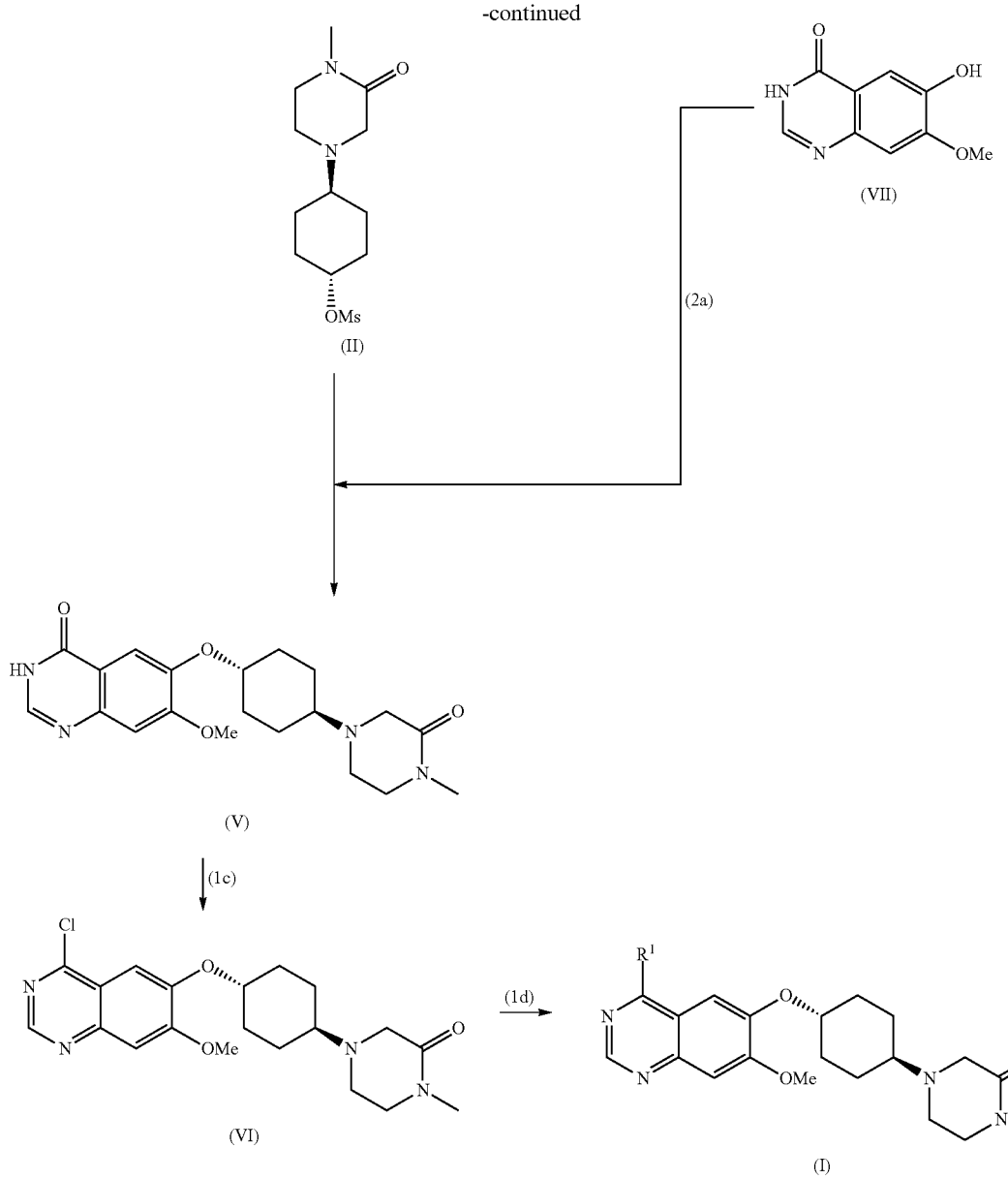

The following Example serves to illustrate the process for preparing the compound of formula (I) carried out by way of example. This Example is to be taken as an illustration of the invention without restricting the latter to its subject-matter.

Preparation of the Compounds According to Scheme 1

2-chloro-N-(2,2-dimethoxy-ethyl)-N-methyl-acetamide

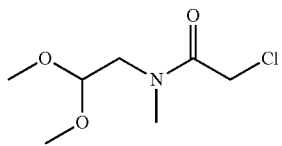

195 ml chloroacetyl chloride in 200 ml 2-methyltetrahydrofuran are added dropwise at 2° C. within one hour to a mixture of 300 ml (methylamino)-acetaldehyde dimethylacetal, 1200 ml 2-methyltetrahydrofuran and 1200 ml saturated potassium carbonate solution. After 40 min 1450 ml of water are added and the phases are separated. The aqueous phase is extracted with 600 ml 2-methyltetrahydrofuran. The combined organic phases are dried on sodium sulphate and evaporated down. 451 g product remain.

Mass spectrum (ESI$^+$): m/z=196 [M+H]$^+$ (trans)-1-hydroxy-4-{[N-(2,2-dimethoxy-ethyl)-N-methyl-amino]-carbonylmethylamino}-cyclohexane

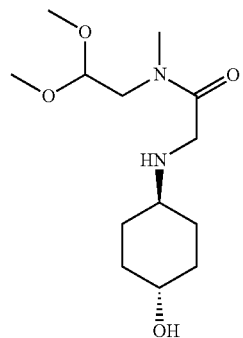

50 g 2-chloro-N-(2,2-dimethoxy-ethyl)-N-methyl-acetamide in 100 ml n-butyl acetate are added dropwise to a suspension of 35.3 g trans-4-aminocyclohexanol and 53 g potassium carbonate in 150 ml n-butyl acetate at 90-100° C. within 2.5 h. After 45 min the suspension is filtered at 65° C. and washed with 70 ml of n-butyl acetate warmed to 65° C. 100 ml solvent are distilled off from the filtrate and the solution evaporated down is inoculated with product at 40° C. After 16 h at ambient temperature the precipitate is filtered off and washed with 70 ml tert-butylmethylether. After drying, 50 g product is obtained.

Mass spectrum (ESI$^+$): m/z=275 [M+H]$^+$ (trans)-1-hydroxy-4-(4-methyl-3-oxo-piperazin-1-yl)-cyclohexane

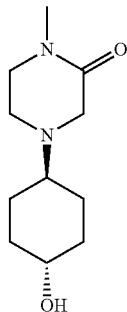

82 g platinum on charcoal (5%) are added to a solution of 822 g (trans)-1-hydroxy-4-{[N-(2,2-dimethoxy-ethyl)-N-methyl-amino]-carbonylmethylamino}-cyclohexane in 4500 ml of methanol and 450 ml of water. After the addition of 499 ml concentrated hydrochloric acid hydrogenation with hydrogen is begun immediately. During the hydrogenation process the mixture is heated to 50° C. After 3 h it is filtered.

This is repeated with another batch of the same size.

The two filtrates from the two batches are combined and poured onto 7100 ml of 30% potassium carbonate solution. At 50° C. the mixture is extracted with 15 L tert-amylalcohol. The aqueous phase is extracted twice more with 7500 ml tert-amylalcohol. 28 L solvent are distilled off from the combined organic phases. 6 L of n-butyl acetate are added and 8 L of solvent are distilled off. 15 L of n-butyl acetate and 1 kg Celite are added and the mixture is heated to 120° C. The solid is filtered off and washed with 5000 ml hot n-butyl acetate. The filtrate is cooled to −5° C. After 3 h the precipitate is filtered off and washed with 5000 ml tert-butylmethylether. After drying, 1025 g of product are obtained. Mass spectrum (ESI$^+$): m/z=213 [M+H]$^+$ Preparation of the Compounds According to Scheme 2 and 3

(trans)-1-methanesulphonyloxy-4-(4-methyl-3-oxo-piperazin-1-yl)-cyclohexane (II)

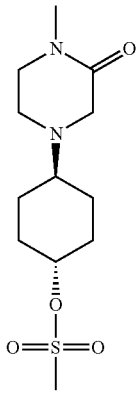

109 g of mesyl chloride in 250 ml THF are added dropwise to 150 g (trans)-1-hydroxy-4-(4-methyl-3-oxo-piperazin-1-yl)-cyclohexane and 162 ml triethylamine in 2300 ml THF in such a way that the temperature does not exceed 35° C. After 25 min the suspension is filtered and washed with 300 ml THF. The filtrate is evaporated down in vacuo at 40° C. to a total mass of 520 g. 230 ml ethyl acetate are added to the suspension. After 15 min the mixture is filtered and the precipitate is washed with 230 ml of ethyl acetate and 150 ml of methyl-tert-butyl ether. After drying, 153.1 g product are obtained.

Mass spectrum (ESI$^+$): m/z=291 [M+H]$^+$ 3-benzyl-3,4-dihydro-4-oxo-6-[trans-4-(4-methyl-3-oxo-piperazin-1-yl)-cyclohexyloxy]-7-methoxy-quinazoline (IV)

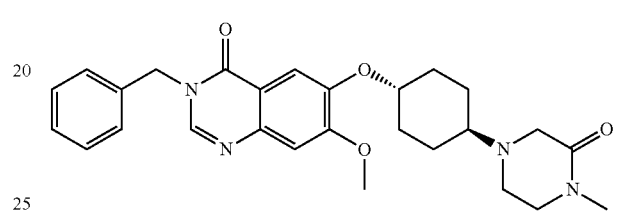

Six times 4.11 g (in total: 24.68 g) of (trans)-1-methanesulphonyloxy-4-(4-methyl-3-oxo-piperazin-1-yl)-cyclohexane (II) are added stepwise at 130° C., within 3.5 h, to 20 g of 3-benzyl-3,4-dihydro-4-oxo-6-hydroxy-7-methoxy-quinazoline (III) and 16.52 g sodium carbonate in 160 ml N-methyl-2-pyrrolidinone. After 19.5 h the reaction mixture is slowly poured into 400 ml of water warmed to 80° C. After 70 min the suspension is filtered off at ambient temperature and the precipitate is washed with water. The moist crude product is dissolved by refluxing in 500 ml of ethanol and 275 ml of water. After cooling to 5° C. and stirring the precipitate is suction filtered and dried. 26.8 g product are obtained.

Mass spectrum (ESI$^+$): m/z=477 [M+H]$^+$ or 88 ml Mesyl chloride are added at 40° C. to 193 g (trans)-1-hydroxy-4-(4-methyl-3-oxo-piperazin-1-yl)-cyclohexane and 168 ml triethylamine in 1710 ml THF. The suspension is filtered so that the filtrate flows directly into 640 ml N-methyl-2-pyrrolidinone. After washing with 1280 ml of warm THF the filtrate is evaporated down in vacuo at 60° C. The oily residue is added batchwise to 214 g 3-benzyl-3,4-dihydro-4-oxo-6-hydroxy-7-methoxy-quinazoline (III) and 177 g sodium carbonate in 640 ml N-methyl-2-pyrrolidinone at 130° C. 340 ml of N-methyl-2-pyrrolidinone are added. After 16 h 2140 ml of water are added at 95° C. After 80 min the precipitate is filtered off and washed with 3000 ml of water. After drying, 346 g product is obtained.

Mass spectrum (ES$^+$): m/z=477 [M+H]$^+$

Spiro[7-azoniabicyclo[2,2,1]heptane-7,4'-[1'-methyl-2'-oxo-4'-piperazinium]]methanesulphonate (VIII)

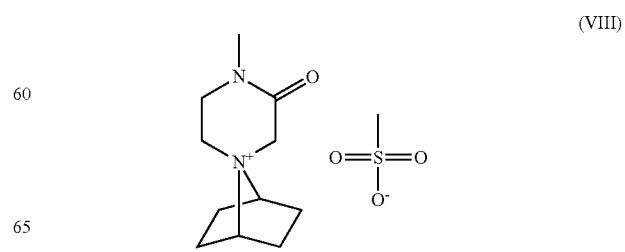

The compound of formula (VIII) is produced as an intermediate product of synthesis step (1a). It can also be prepared by storing 350 mg of (trans)-1-methanesulphonyloxy-4-(4-methyl-3-oxo-piperazin-1-yl)-cyclohexane (II) for 15.5 h in the vacuum drying oven at 110° C. 350 mg of new product of the compound of formula (VIII) are formed.

Mass spectrum (ESI⁺): m/z=195 [M]⁺

3,4-dihydro-4-oxo-6-[trans-4-(4-methyl-3-oxo-piperazin-1-yl)-cyclohexyloxy]-7-methoxy-quinazoline hydrochloride [(V) HCl]

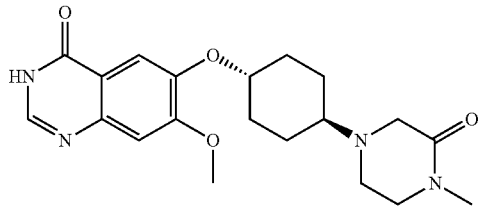

355 g of 3-benzyl-3,4-dihydro-4-oxo-6-[trans-4-(4-methyl-3-oxo-piperazin-1-yl)-cyclohexyloxy]-7-methoxy-quinazoline are hydrogenated for 23 hours at 80° C. in a solution of 1775 ml of water and 1065 ml glacial acetic acid with 35.5 g palladium on charcoal (10% Pd). The catalyst is filtered off and washed with 500 ml of water. 950 ml of 50% sodium hydroxide solution are added. 3000 ml of tert-amylalcohol are added to the suspension and the phases are separated. The aqueous phase is extracted with 3000 ml tert-amylalcohol. The combined organic phases are evaporated down and the residue is dissolved in 3000 ml of ethanol at 78° C. 76 ml of HCl in ethanol (10 mol/L) are added. After inoculation with product hydrochloride and cooling to -3° C. the precipitate is suction filtered and washed with 200 ml of ethanol and 800 ml methyl-tert-butyl ether. After drying 266 g of product is obtained as the hydrochloride.

Mass spectrum (ES⁺): m/z=387 [M+H]⁺ or

3,4-dihydro-4-oxo-6-[trans-4-(4-methyl-3-oxo-piperazin-1-yl)-cyclohexyloxy]-7-methoxy-quinazoline (V)

2.4 g sodium carbonate are added to 2 g of 3,4-dihydro-4-oxo-6-hydroxy-7-methoxy-quinazoline (VII) in 16 ml N-methyl-2-pyrrolidinone at 130° C. Then six times 600 mg (in total: 2.4 g) (trans)-1-methanesulphonyloxy-4-(4-methyl-3-oxo-piperazin-1-yl)-cyclohexane (II) are added stepwise at 130° C. within 4 h and the mixture is kept at 130° C. for 20 h. After 10 days, 25 ml of water are added and the mixture is extracted with 25 ml isopropyl acetate, 50 ml of dichloromethane and 25 ml of dichloromethane. The organic phases are evaporated down and the residue is separated off by preparative HPLC. 500 mg of the product are obtained.

Mass spectrum (ES⁺): m/z=387 [M+H]⁺

4-chloro-6-[trans-4-(4-methyl-3-oxo-piperazin-1-yl)-cyclohexyloxy]-7-methoxy-quinazoline hydrochloride [(VI)HCl]

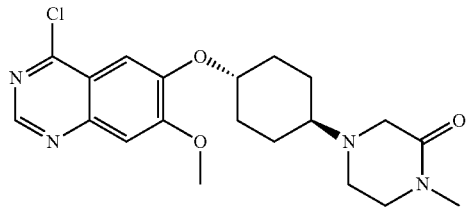

210 g of 3,4-dihydro-4-oxo-6-[trans-4-(4-methyl-3-oxo-piperazin-1-yl)-cyclohexyloxy]-7-methoxy-quinazoline hydrochloride [(V) HCl] in 1680 ml acetonitrile are refluxed and 840 ml of solvent are distilled off (elimination of traces of water). 221.4 g triphenylphosphine in 840 ml dioxane are added. 119.4 g of N-chlorosuccinimide in 600 ml acetonitrile are added. 260 ml acetonitrile are added. The mixture is stirred for 45 min at 80° C. and then cooled to 30° C. 8.94 ml of water and 420 ml dioxane are added. The precipitate is filtered off under protective gas and washed with 1200 ml THF. The product is precipitated as the hydrochloride and is processed further without drying. A small amount was dried and the yield can be calculated as approx. 210 g in relation thereto.

Mass spectrum (ES⁺): m/z=405 [M+H]⁺

4-[(3-chloro-2-fluoro-phenyl)amino]-6-[trans-4-(4-methyl-3-oxo-piperazin-1-yl)-cyclohexyloxy]-7-methoxy-quinazoline [According to General Formula (I)]

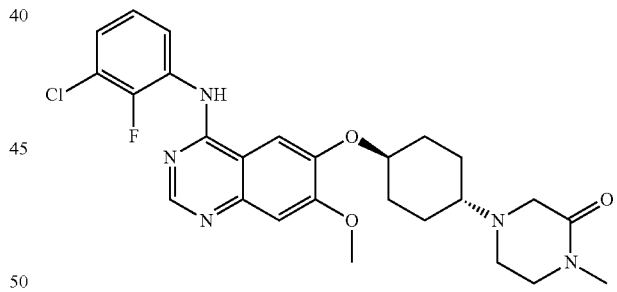

400 g of crude 4-chloro-6-[trans-4-(4-methyl-3-oxo-piperazin-1-yl)-cyclohexyloxy]-7-methoxy-quinazoline (VI) (taken directly from the previous synthesis; still contains THF—corresponds to approx. 210 g of 4-chloro-6-[trans-4-(4-methyl-3-oxo-piperazin-1-yl)-cyclohexyloxy]-7-methoxy-quinazoline hydrochloride) are added to 86.7 g of 3-chloro-2-fluoroaniline in 2200 ml of 2N hydrochloric acid at 20° C. After 1 h 2200 ml of toluene are added and the mixture is heated to 65° C. for 1 h. The mixture is stirred for 19 h at ambient temperature and then for 1 h at 6° C. The precipitate is suction filtered and washed with 400 ml of 2N hydrochloric acid and 400 ml of toluene. After drying the crude product is obtained as the hydrochloride or dihydrochloride. This is dissolved in 1900 ml of water and 1900 ml of ethanol. 920 ml of 1N NaOH are added and 1000 ml of solvent are distilled off. The mixture is inoculated with product and 740 ml solvent are distilled off. After cooling to 7° C. the precipitate is washed with 1000 ml of water and dried. The precipitate is dissolved in 7400 ml of ethanol at 78° C. 50 g of activated charcoal are added and the solution is filtered and washed with 900 ml of hot ethanol. 5300 ml are distilled off from the solution. It is inoculated with product and 1000 ml of solvent are distilled off. After stirring for 66 h at ambient temperature the precipitate is filtered off and washed with 500 ml of ethanol. After drying, 191 g of product are obtained.

Mass spectrum (ESI+): m/z=514 [M+H]+

Compounds of general formula (I) are prepared analogously to the procedure described above.

The invention claimed is:

1. A process for the stereoselective preparation of compounds of formula (I)

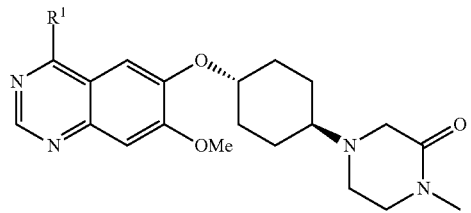

(I)

optionally in the form of the tautomers thereof, and optionally the pharmacologically acceptable acid addition salts thereof, wherein
R$^1$ denotes a group selected from among 3-chloro-2-fluoro-phenyl-amino, 3-chloro-4-fluoro-phenylamino, 2-fluoro-3-methyl-phenylamino, 2,5-difluoro-3-methyl-phenylamino, 3-chloro-2-methyl-phenylamino- and 2-fluoro-5-methyl-phenylamino,
characterised in that the process comprises reaction steps (1a) to (1d), wherein (1a) is the reaction of a compound of formula (II)

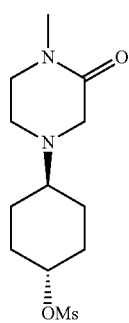

(II)

with a compound of formula (III)

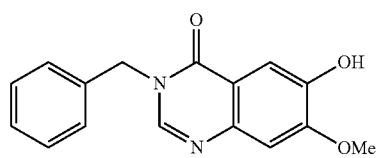

(III)

to form a compound of formula (IV)

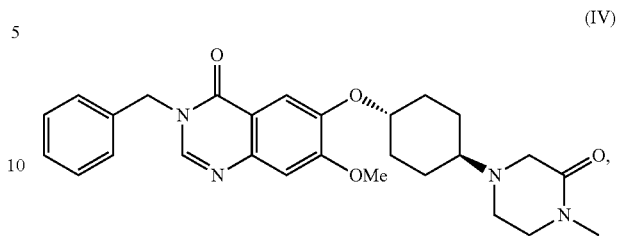

(IV)

(1b) is the cleaving of the benzyl group of the compound of formula (IV) in the presence of a catalyst to form a compound of formula (V)

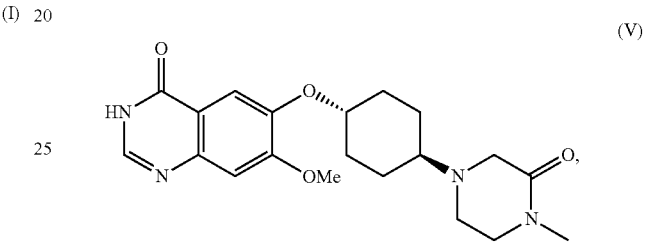

(V)

(1c) is the reaction of the compound of formula (V) with a chlorinating agent to form the hydrochloride of a compound of formula (VI)

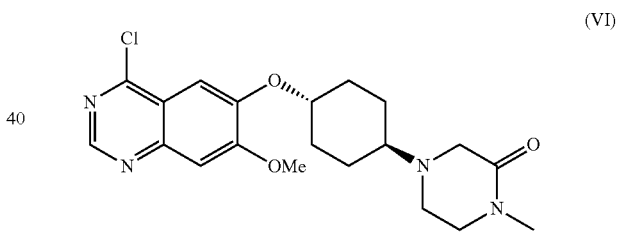

(VI)

and (1d) is the reaction of the compound of formula (VI) with one of the compounds (i) to (vi) to form a compound of formula (I),
wherein
(i) is 3-chloro-2-fluoro-aniline,
(ii) is 3-chloro-4-fluoro-aniline,
(ii) is 2-fluoro-3-methyl-aniline,
(iii) is 2,5-difluoro-3-methyl-aniline,
(iv) is 3-chloro-2-methyl-aniline, and
(vi) is 2-fluoro-5-methyl-aniline,
while steps (1a) to (1d) take place successively in the order specified, or
characterised in that the process comprises reaction steps (2a), (1c) and (1d) wherein (2a) is the reaction of a compound of formula (II)

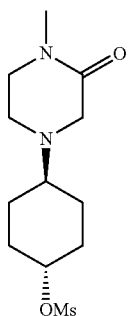

with a compound of formula (VII)

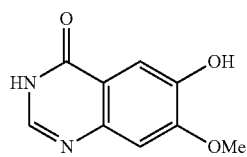

to form a compound of formula (V)

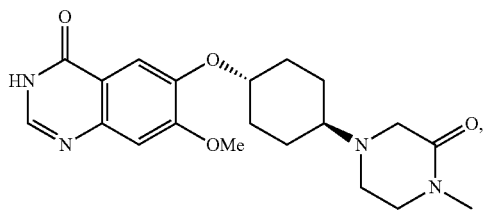

while the steps take place successively in the order specified.

2. The process according to claim 1 for the stereoselective preparation of compounds of general formula (I), characterised in that the process consists of process steps (1a) to (1d).

3. The process according to claim 1 for the stereoselective preparation of compounds of general formula (I), characterised in that it consists of process steps (2a), (1c) and (1d).

4. The process according to claim 1 for the stereoselective preparation of compounds of general formula (IV), characterised in that the process consists of process step (1a).

5. The process according to claim 1 for the stereoselective preparation of compounds of general formula (V), characterised in that the process consists of process step (1b).

6. The process according to claim 1 for the stereoselective preparation of compounds of general formula (VI), characterised in that the process consists of process step (1c).

7. The process according to claim 1 for the stereoselective preparation of compounds of general formula (I), characterised in that the process consists of process step (1d).

8. The process according to claim 1 for the stereoselective preparation of compounds of general formula (IV), characterised in that the process consists of process step (2a).

9. The compound of formula (II)

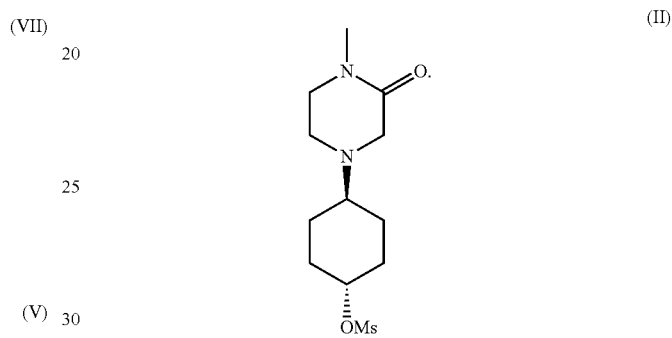

10. The compound of formula (VIII)

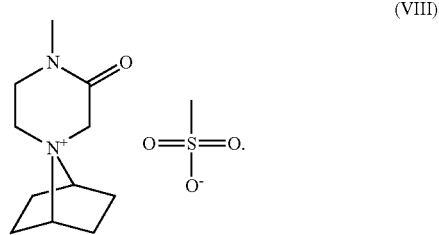

* * * * *